(12) United States Patent
Hara et al.

(10) Patent No.: US 6,232,411 B1
(45) Date of Patent: May 15, 2001

(54) HYDROGENATED DIGLYCIDYL ETHERS OF BIPHENY-4,4'-DIOL

(75) Inventors: Yoshinori Hara, Yokohama; Mareki Miura; Yoshinobu Ohnuma, both of Yokkaichi; Hiroko Takahashi, Yokohama, all of (JP)

(73) Assignee: Mitsubishi Chemical Co., Tokyo ( * ) Notice: Subject to any disclaimer, the term of this patent is extended or adjusted under 35 U.S.C. 154(b) by 0 days.

(21) Appl. No.: 09/322,633

(22) Filed: May 28, 1999

(30) Foreign Application Priority Data

May 29, 1998 (JP) .................................................. 10-164404

(51) Int. Cl.$^7$ .................................................. C08G 59/06
(52) U.S. Cl. .................................. 525/523; 528/87; 528/98
(58) Field of Search ............................... 525/523; 528/87, 528/98

(56) References Cited

FOREIGN PATENT DOCUMENTS

1243045 * 10/1988 (CA) .

* cited by examiner

*Primary Examiner*—Robert E. L. Sellers
(74) *Attorney, Agent, or Firm*—Y. Grace Tsang

(57) ABSTRACT

An epoxy compound formula (1), and a hydrogenation process for preparing thereof;

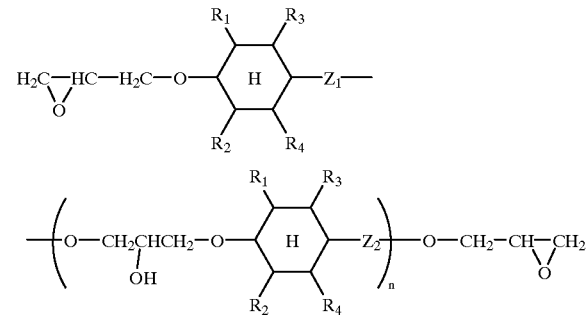

wherein $R_1$ to $R_4$ each represent a hydrogen atom or an alkyl group having 1 to 6 carbon atoms; n represents an integer of 0 to 6; and $Z_1$ and $Z_2$ each represent a phenyl group substituted or unsubstituted by one or more alkyl groups or a cyclohexyl group substituted or unsubstituted by one or more alkyl groups.

16 Claims, 2 Drawing Sheets

HYDROGENATED DIGLYCIDYL ETHERS OF BIPHENY-4,4'-DIOL

FIELD OF THE INVENTION

The present invention relates to a novel epoxy compound and a method of preparing the same. More particularly, the present invention relates to a novel epoxy compound that provides excellent workability because the compound is liquid or a solid having a low melting point, and can be used as resins for encapsulation of semiconductors, laminates, coatings, adhesives, casting materials and electrical insulation materials.

BACKGROUND OF THE INVENTION

Epoxy resins have been employed in a variety of fields because of their excellent properties such as heat resistance, adhesion, water resistance, mechanical strength and electrical properties. Especially in electrical and electronic fields, epoxy resins have found widespread use as electrical insulation castings, laminating materials and materials for encapsulation. However, in recent years, with the miniaturization, high precision and high performance of electrical and electronic components, there has been a demand for molding properties, high moisture resistance and high electrical properties of epoxy resins to be used.

For example, recently, LSI packaging is showing the trend of high density and thin shape, with the development of portable devices such as IC cards, LCDs, portable telephones and note-type personal computers, and is changing the process thereof from the conventional transfer-molding packaging to so-called COB (chip-on-board) or TAB processes in which bare chips are mounted and are encapsulated with liquid encapsulating materials. The epoxy resins that are made from bisphenol A or bisphenol F are main streams of the conventional epoxy resins for liquid encapsulation. However, there has been a demand for the improvement of reliability of liquid encapsulating materials because these resins have poor moisture resistance and poor heat resistance.

A method has been proposed in which biphenyl type crystalline epoxy resins having low stress, low moisture absorption, and excellent crack-resistance in soldering, which are used in large quantities as LSI-packaging materials for transfer molding use, or to make the resins have a low melting point, is liquefied or subjected to have a low melting point (confer Japanese Unexamined Patent Publication No. Sho 07-62060). However, in this method, since considerably large amounts of phenol compounds or compounds having carboxyl groups are subjected to a reaction with biphenyl type epoxy resins, obtained epoxy resins do not have satisfactory curing characteristics and cured resins therefrom do not have satisfactory heat resistance.

SUMMARY OF THE INVENTION

The present invention has been made to solve the above-mentioned problem, and an object of the present invention is to provide a novel liquid or low-melting-solid epoxy compound having low melt viscosity which conventional epoxy compounds do not have and being capable of giving cured resins with a good balance between moisture resistance and heat resistance.

The present invention relates to a novel epoxy compound that is obtained by hydrogenation of a biphenyl-type aromatic epoxy compound, and to a method of preparing the same. The present invention comprises the following aspects of the invention.

(1) An epoxy compound represented by general formula (1);

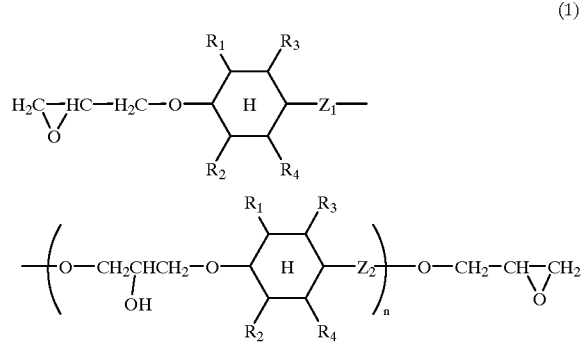

wherein $R_1$ to $R_4$ each represent a hydrogen atom or an alkyl group having 1 to 6 carbon atoms; n represents an integer of 0 to 6 and $Z_1$ and $Z_2$ each represent general formula (2) or (3);

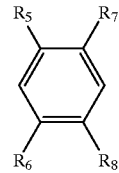

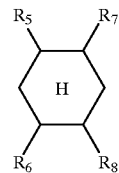

wherein $R_5$ to $R_8$ each represent a hydrogen atom or an alkyl group having 1 to 6 carbon atoms.

(2) A method of preparing an epoxy compound represented by general formula (1);

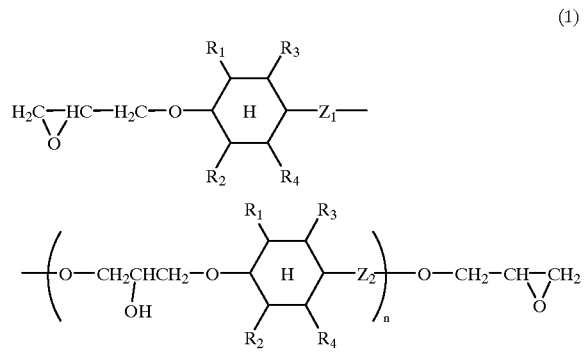

wherein $R_1$ to $R_4$ each represent a hydrogen atom or an alkyl group having 1 to 6 carbon atoms; n represents an integer of 0 to 6 and $Z_1$ and $Z_2$ each represent general formula (2) or (3);

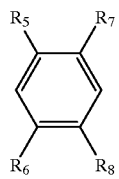
(2)

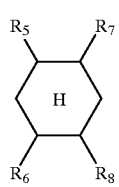
(3)

wherein $R_5$ to $R_8$ each represent a hydrogen atom or an alkyl group having 1 to 6 carbon atoms, which is characterized by hydrogenation of an aromatic epoxy compound represented by general formula (4);

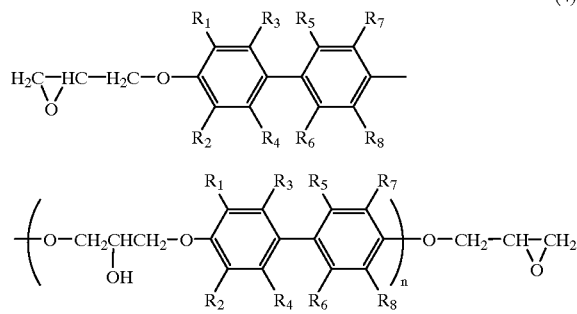
(4)

wherein $R_1$ to $R_8$ each represent a hydrogen atom or an alkyl group having 1 to 6 carbon atoms and n represents an integer of 0 to 6.

(3) A method of preparing an epoxy compound as described in the item (2), characterized in that the hydrogenation is a reaction preparing an epoxy compound represented by general formula (1) by hydrogenating the aromatic epoxy compound represented by general formula (4) dissolved in an ether-based solvent under pressure in the presence of a catalyst in which rhodium or ruthenium is carried on a graphite.

(4) A method of preparing an epoxy compound as described in the item (2) or (3), characterized in that the hydrogenation is a reaction hydrogenating the aromatic epoxy compound represented by general formula (4) to such an extent that a hydrogenation rate of aromatic rings of the aromatic epoxy compound becomes 10 to 100%.

(5) A method of preparing an epoxy compound as described in any one of the items (2) to (4), characterized in that the hydrogenation is a reaction hydrogenating the aromatic epoxy compound of general formula (4) to such an extent that a hydrogenation rate of aromatic rings of the aromatic epoxy compound becomes 20 to 90%.

(6) A method of preparing an epoxy compound as described in any one of the items (2) to (5), characterized in that an aromatic epoxy compound represented by general formula (4) is an aromatic epoxy compound represented by general formula (4); wherein $R_1$, $R_2$, $R_7$ and $R_8$ each represent a hydrogen atom or a methyl group; $R_3$, $R_4$, $R_5$ and $R_6$ each represent a hydrogen atom and n represents an integer of 0 to 3.

(7) A curing composition characterized by containing one or two or more of epoxy compounds represented by general formula (1) in the item (1) and curing agents for epoxy compounds.

DETAILED EMBODIMENT OF THE INVENTION

Figure 1:
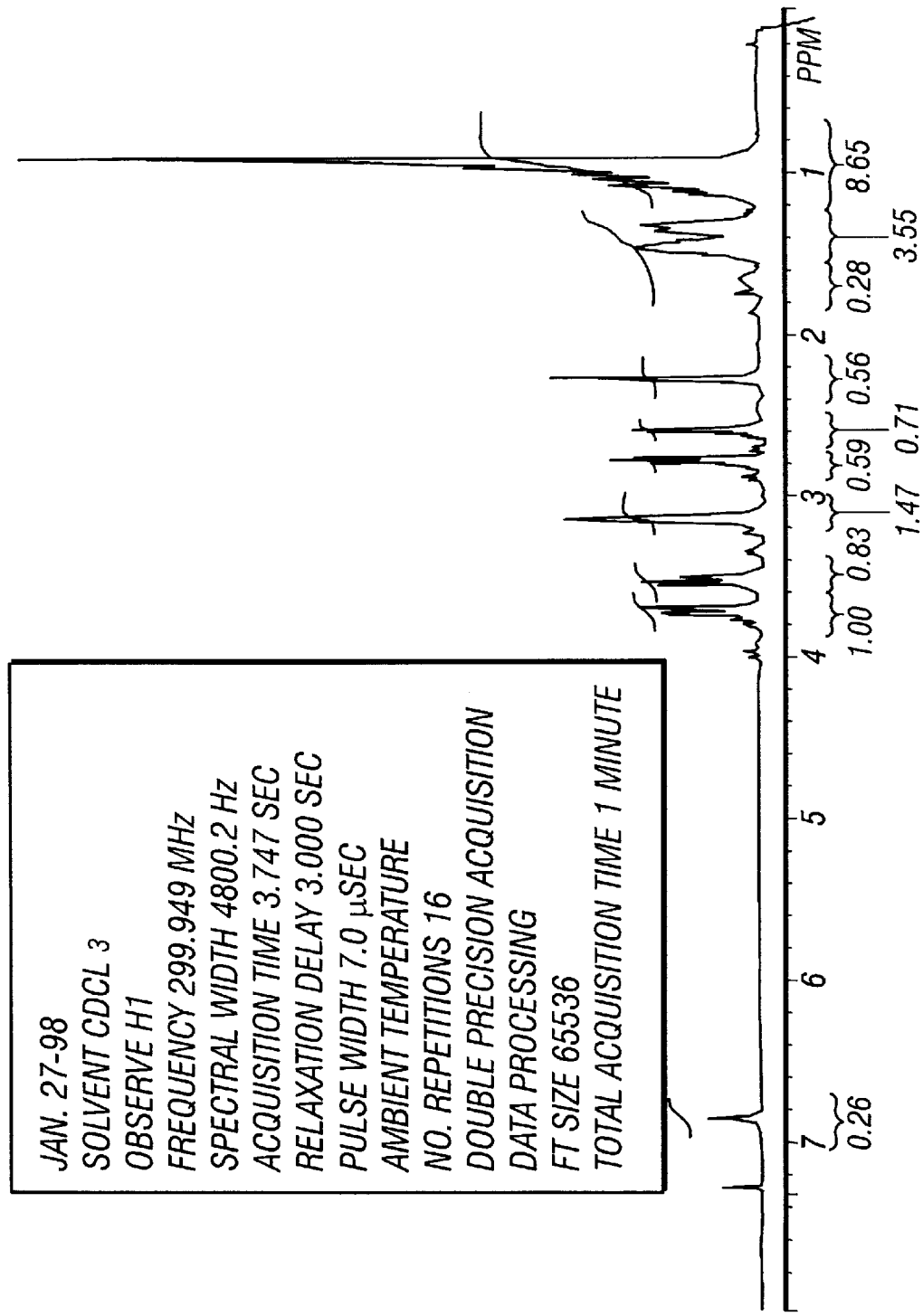
FIG. 1 shows a nuclear magnetic resonance spectrum of the epoxy compound in accordance with Example 1.

A novel epoxy compound according to the present invention is an epoxy compound represented by general formula (1), and comprises a hydrogenated epoxy compound that contains an epoxy compound of which aromatic rings are completely hydrogenated, represented by the following general formula (5) and/or an epoxy compound half of which aromatic rings are hydrogenated, represented by the following general formula (6).

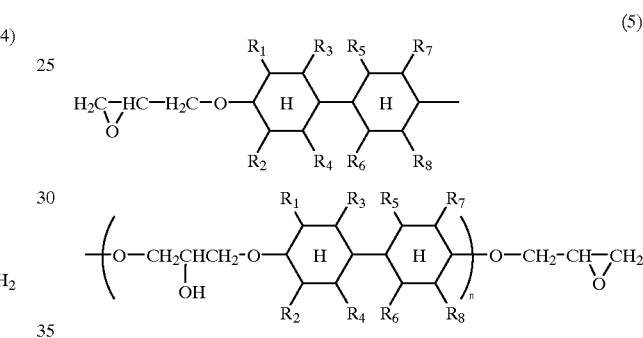
(5)

(In the formula, $R_1$ to $R_8$ and n are the same as described above)

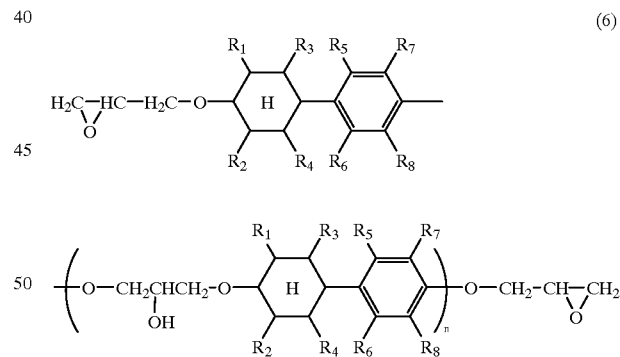
(6)

(In the formula, $R_1$ to $R_8$ and n each are the same as described above)

The epoxy compound of the present invention, represented by general formula (1), may contain the remaining material, an aromatic epoxy compound represented by general formula (4). The hydrogenation rate of aromatic rings of the epoxy compound obtained by carrying out the present invention is within a range from 10 to 100%, and is preferably within a range from 20 to 90% to obtain a liquid epoxy compound.

A method of preparing an epoxy compound according to the present invention is attained by selectively hydrogenating aromatic rings of an aromatic epoxy compound represented by general formula (4) in the presence of a catalyst by the well-known method. A preferable reaction procedure comprises: dissolving the aromatic epoxy compound in an ethers solvent such as tetrahydrofuran or dioxane and selectively hydrogenating the aromatic rings in the presence of a catalyst in which rhodium or ruthenium is carried on a graphite. The surface area of the graphite is within a range from 10 m$^2$/g to 400 m$^2$/g, preferably within a range from 50 m$^2$/g to 300 m$^2$/g. The reaction conditions are appropriately selected from the following: in a pressure range from 1 to 30 MPa, preferably 3 to 15 MPa, in a temperature range from 30 to 150°, preferably 50 to 120°, and in a reaction time range from 0.5 to 20 hours, preferably 1 to 10 hours. After the completion of the reaction, the catalyst is removed by filtration, and the ethers organic solvent is distilled out under reduced pressure until it becomes substantially absent to obtain an epoxy compound with the hydrogenated aromatic rings.

Synthesis of an aromatic epoxy compound represented by general formula (4) as material is conducted by the well-known reaction method in which a biphenol compound represented by the following general formula (7) is subject to a reaction with epihalohydrin and base (wherein $R_1$ to $R_8$ each represent a hydrogen atom or an alkyl group having 1 to 6 carbon atoms).

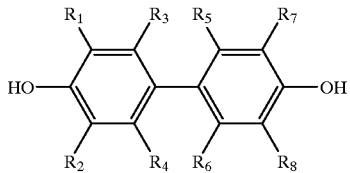

(7)

Specific examples of biphenol represented by general formula (7), which is used to prepare an aromatic epoxy compound represented by general formula (4), which is the material to prepare an epoxy resin represented by general formula (1) of the present invention, includes, biphenol, 3,3'-dimethylbiphenyl-4,4'-diol, 3,3'-ditert-butylbiphenyl-4,4'-diol, 3,3',5,5'-tetramethylbiphenyl-4,4'-diol, 2,2'-ditert-butyl-5,5'-dimethylbiphenyl-4,4'-diol, 3,3'-ditert-butyl-5,5'-dimethylbiphenyl-4,4'-diol, 3,3',5,5'-tetratert-butylbiphenyl-4,4'-diol, 2,2',3,3',5,5'-hexamethylbiphenyl-4,4'-diol, 2,2',3,3',5,5',6,6'-octamethylbiphenyl-4,4'-diol, 3,3'-di-n-hexylbiphenyl-4,4'-diol, 3,3'-di-n-hexyl-5,5'-dimethylbiphenyl-4,4'-diol and the like.

Among the above-mentioned biphenol compounds, a biphenol compound of general formula (7) wherein $R_1$, $R_2$, $R_7$ and $R_8$ each represent a hydrogen atom or a methyl group, and $R_3$, $R_4$, $R_5$ and $R_6$ each represent a hydrogen atom, is preferable on account of that the material thereof is easily available and cured resins having an excellent heat resistance can be obtained.

Moreover, an aromatic epoxy compound of general formula (4) wherein n is an integer of 0 to 3, is preferred to be used as the material for preparing an epoxy compound in a sense that the melt viscosity of the resulting epoxy compound is lowered, and the reactivity with curing agents is excellent.

The obtained epoxy compound is a liquid compound at room temperature or a compound having a melting point of 80° C. or below. Accordingly, reactions with various kinds of curing agents may give the harder cured resins.

As curing agents for the hydrogenated epoxy compound of the present invention, general curing agents used for epoxy compounds may be used. Examples of such curing agents include amines, carboxylic acid anhydrides, polyphenols, imidazole-based compounds, BF$_3$ complex compounds of amines, salts of Brönsted acids such as sulfonium salts, hydrazide compounds of organic acids, polymercaptans and organic phosphine compounds. Of these, respective ones or two or more kinds thereof can be used in combination.

The amount of the curing agents used is within a range from 0.01 to 200 parts by weight, preferably within a range from 0.1 to 150 parts by weight based on 100 parts by weight of the novel epoxy compound (resin).

In order to obtain the cured resins according to the epoxy compound of the invention, powdered reinforcing materials and fillers may optionally be added thereto.

Examples of the reinforcing material and filler include, metal oxides such as aluminum oxide and magnesium oxide, metal carbonates such as calcium carbonate or magnesium carbonate, silicon compounds such as powdered diatomaceous earth and fused silica, and metal hydroxides such as aluminum hydroxide. Also, kaoline, mica, graphite, etc, and fibrous reinforcing materials and fillers such as fiber glass, ceramic fibers, carbon fibers, alumina fibers, silicon carbide fibers, boron fibers, polyester fibers, polyamide fibers and the like may be used. These materials are mixed within a range from 10 to 900 parts by weight based on 100 parts by weight of the total of the epoxy compound and the curing agents.

Coloring agents, pigments and flame-retardant such as titanium dioxide, iron black, molybdenum red, navy blue, ultramarine blue, cadmium yellow, cadmium red, antimony trioxide, red phosphorus, brominated compounds, triphenylphosphate may be added thereto. These are mixed within a range from 0.1 to 20 parts by weight based on 100 parts by weight of the total of the epoxy compounds and the curing agents.

Further, a variety of curable monomers, oligomers, polymers and the like may be also mixed to improve the qualities of coatings, adhesive layers and molded resins, which are the cured resins made from the improved epoxy compound of the present invention.

EXAMPLES

Hereinafter, an epoxy compound and a method of preparing the same according to the present invention are explained in more detail by referring to examples and comparative examples. It is to be noted that "part" in the examples means "part by weight."

Example 1

A 500-milliliter autoclave equipped with an agitator, a condenser and a thermometer was charged with 100 g of Epikote YX4000 (a trade name of Yuka Shell Epoxy KK: a diglycidyl ether of 3,3',5,5'-tetramethylbiphenyl-4,4'-diol, an epoxy equivalent is 185 g/eq.), 100 g of tetrahydrofuran, and 4.0 g of a catalyst (the surface area of graphite: 130 m$^2$/g) composed of 5 wt %-rhodium/95 wt %-graphite, followed by conducting a reducing reaction for 9 hours while maintaining the conditions of a hydrogen pressure of 7 MPa, a temperature of 70° C., and an agitation speed of 500 to 800 rpm. After the completion of the reaction, the autoclave was cooled and the catalyst was filtered, followed by distilling out tetrahydrofuran under reduced pressure and at a temperature of 50° C. with an evaporator to obtain 96.9 g of a epoxy compound (resin) which is a yellow solid.

With respect to the properties of the epoxy compound, the melting point was 58° C., the loss rate of epoxy groups measured by a titration method with perchloric acid was 9.6% and the hydrogenation rate of an aromatic rings measured by a nuclear magnetic resonance analysis was 94%.

The nuclear magnetic resonance spectrum shown in FIG. 1 and a FAB mass spectrum were used to confirm whether the obtained compound is the desired one.

The nuclear magnetic resonance spectrum 0.8 to 1.8 ppm: Protons of cyclic rings or methyl groups connected with cyclic rings 2.5 to 2.6 ppm and 2.7 to 2.8 ppm:
Methylene protons of epoxy rings
3.0 to 3.2 ppm: Methylene protons of epoxy rings
3.45 to 3.6 ppm and 3.65 to 3.8 ppm:
Methylene protons of glycidyl ether groups
The FAB mass spectrum
Epoxy compounds with completely hydrogenated aromatic rings:

366 (the component of general formula (5), wherein n=0)
676 (the component of general formula (5), wherein n=1)
Epoxy compounds with aromatic rings, half of which were hydrogenated:

360 (the component of general formula (6), wherein n=0)
Each of the above fragment peaks was confirmed.

Example 2

Figure 2:
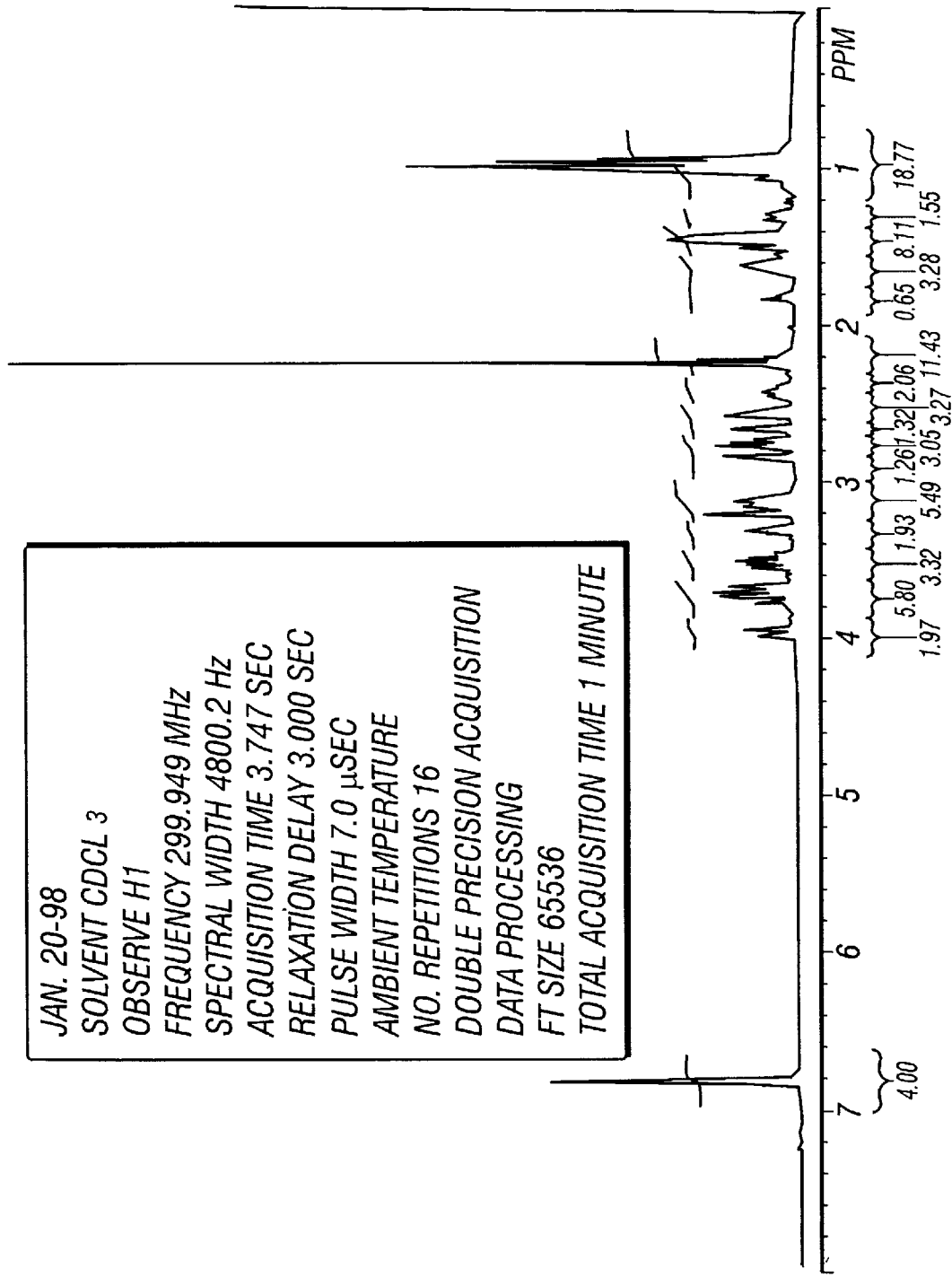
FIG. 2 shows a nuclear magnetic resonance spectrum of the epoxy compound in accordance with Example 2.

The same operations were followed as in the above-described Example 1, except that the hydrogenating reaction time was changed to 3 hours to obtain 96.1 g of epoxy compound that is a yellow and transparent liquid. The nuclear magnetic resonance spectrum shown in FIG. 2 was used to confirm whether the obtained compound is the desired one or not. Properties of the obtained epoxy compound are shown in Table 1.

Example 3

The same operations were followed as in the above-described Example 1, except that the material of aromatic epoxy compound was changed to 100 g of YL6121H (a trade name of Yuka Shell Epoxy KK: a mixture of a diglycidyl ether of 3,3',5,5'-tetramethylbiphenyl-4,4'-diol and a diglycidyl ether of 4,4'-biphenol, an epoxy equivalent is 171 g/eq.) to obtain 97.3 g of epoxy compound that is a light yellow solid. Properties of the obtained epoxy compound are also shown in Table 1.

Example 4

The same operations were followed as in the above-described Example 2, except that the material of aromatic epoxy compound was changed to 100 g of YL6121H to obtain 96.8 g of epoxy compound that is a light yellow and transparent liquid. Properties of the obtained epoxy compound are also shown in Table 1.

TABLE 1

| Epoxy Compound | | Example 1 YX4000 100 parts | Example 2 YX4000 100 parts | Example 3 YL6121H 100 parts | Example 4 YL6121H 100 parts |
|---|---|---|---|---|---|
| Hydrogenation rate (%) *1 | | 94 | 62 | 97 | 53 |
| Melting point (° C.) *2 | | 58 | Liquid | 52 | Liquid |
| The components of epoxy compounds (%) *3 | Aromatic ring completely hydrogenated epoxy | 72.7 | 23.1 | 79.5 | 16.4 |
| | Aromatic ring Half hydrogenated aromatic epoxy compound | 12.1 | 60.4 | 7.1 | 61.6 |
| | Residual aromatic Epoxy compound | Not detected | 5.3 | Not detected | 12.5 |
| | The other Compounds*4 | 15.2 | 11.2 | 13.4 | 9.5 |
| GPC (%) n = 0 *5 | | 85.6 | 86.9 | 86.1 | 87.7 |

Notes:
*1: The residual rate of aromatic rings measured from a nuclear magnetic resonance spectrum
*2: The peak temperature of heat absorption measured from DSC (the temperature rising rate: 10° C./minute)
*3: The percentage by area of the components measured from a liquid chromatograph (RI detector)
*4: The compounds of which epoxy groups were hydrogenated, saponifiable chlorinated compounds or the like
*5: GPC was measured from the percentage by area of a gel permeation chromatograph and shows the rate of the components of general formulas (1) and (4), wherein n = 0.

By effecting the present invention, a novel epoxy compound can be easily prepared by hydrogenating an aromatic epoxy compound which has biphenyl type structure. The epoxy compound provides excellent workability because the compound is liquid at a room temperature or a solid having a low melting point, and is applicable to wider uses. Especially in electric and electronic fields such as encapsulants for semiconductors, casting materials and electric insulating materials.

What is claimed is:

1. An epoxy compound represented by general formula (1);

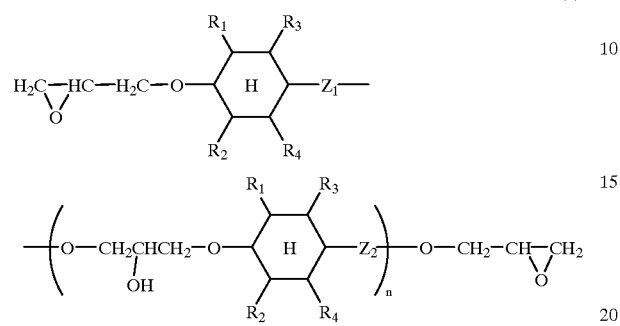

wherein $R_1$ to $R_4$ each represent a hydrogen atom or an alkyl group having 1 to 6 carbon atoms; n represents an integer of 0 to 6; and $Z_1$ and $Z_2$ each represent general formula (2) or (3):

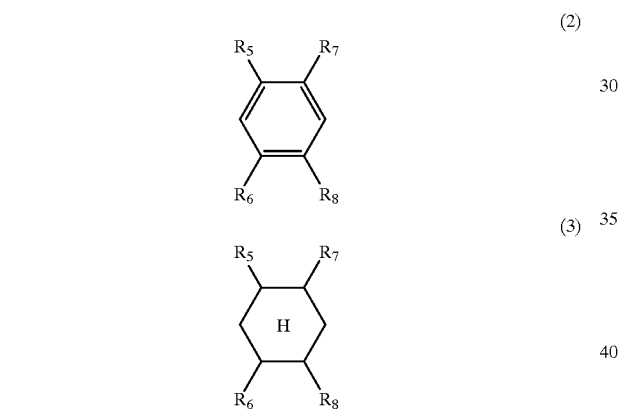

wherein $R_5$ to $R_8$ each represent a hydrogen atom or an alkyl group having 1 to 6 carbon atoms; and wherein 10% to 90% of $Z_1$ and $Z_2$ have the general formula (2).

2. A method for preparing an epoxy compound represented by general formula (1);

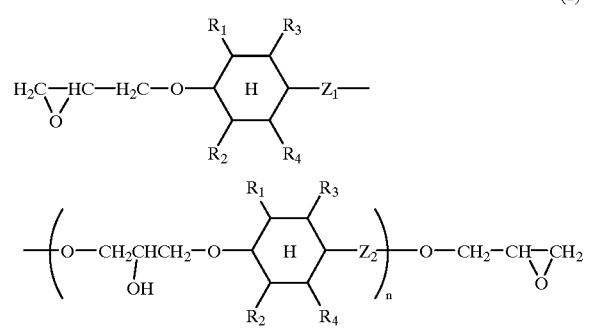

wherein $R_1$ to $R_4$ each represent a hydrogen atom or an alkyl group having 1 to 6 carbon atoms; n represents an integer of 0 to 6 and $Z_1$ and $Z_2$ each represent general formula (2) or (3);

wherein $R_5$ to $R_8$ each represent a hydrogen atom or an alkyl group having 1 to 6 carbon atoms, comprising: hydrogenating from 10% to 90% of the aromatic groups in an aromatic epoxy compound represented by general formula (4);

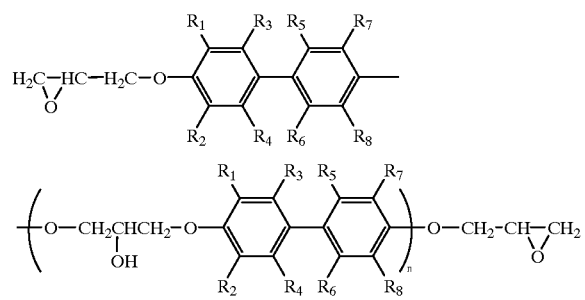

wherein $R_1$ to $R_8$ each represent a hydrogen atom or an alkyl group having 1 to 6 carbon atoms and n represents an integer of 0 to 6.

3. The method as claimed in claim 2, wherein the aromatic epoxy compound represented by general formula (4) is dissolved in an ether-based solvent, and the resulting mixture is hydrogenated under pressure in the presence of a catalyst in which rhodium or ruthenium is carried on a graphite.

4. The method of preparing an epoxy compound as claimed in claim 1, wherein from 20 to 90% of the aromatic epoxy compound is hydrogenated.

5. The method of preparing an epoxy compound as claimed in claim 4, wherein $R_1$, $R_2$, $R_7$ and $R_8$ each represent a hydrogen atom or a methyl group; $R_3$, $R_4$, $R_5$ and $R_6$ each represent a hydrogen atom; and n represents an integer of 0 to 3.

6. The epoxy compound of claim 1, wherein n represents an integer of 0 to 3.

7. The epoxy compound of claim 1, wherein $R_1$, $R_2$, $R_7$, and $R_8$ each represent a hydrogen atom or a methyl group.

8. The epoxy compound of claim 1, wherein $R_1$, $R_2$, $R_7$, and $R_8$ each represent a methyl group and $R_3$, $R_4$, $R_5$ and $R_6$ each represent a hydrogen atom.

9. The epoxy compound of claim 1, wherein n=0 and $Z_1$ represents general formula (2).

10. An epoxy compound represented by general formula (1);

(1)

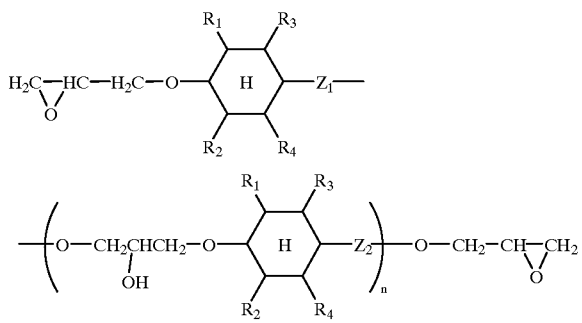

wherein $R_1$ and $R_2$ each represent an alkyl group having 1 to 6 carbon atoms; $R_3$, and $R_4$, each represent a hydrogen atom; n represents an integer of 0 to 6; and $Z_1$ and $Z_2$ each represent general formula (2) or (3), wherein from 10% to 90% of $Z_1$ and $Z_2$ have the structure (2)

(2)

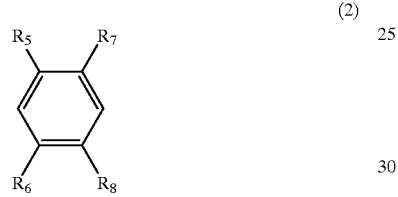

(3)

wherein $R_7$ and $R_8$ each represent an alkyl group having 1 to 6 carbon atoms; and $R_5$ and $R_6$ each represent a hydrogen atom.

11. The epoxy compound of claim 10, wherein $R_1$, $R_2$, $R_7$, and $R_8$ each represent a methyl group.

12. The epoxy compound of claim 10, wherein n represents an integer of 0 to 3.

13. An epoxy compound represented by general formula (1):

(1)

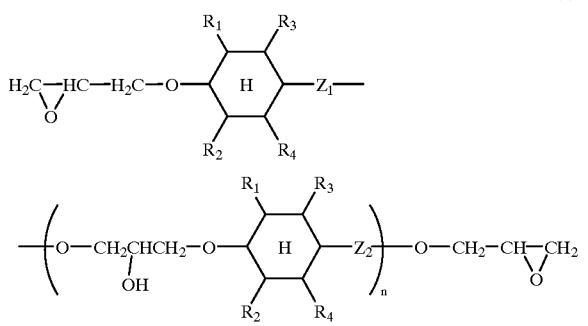

wherein $R_1$ to $R_4$ each represent a hydrogen atom or an alkyl group having 1 to 6 carbon atoms; n represents an integer of 0 to 6 and $Z_1$ and $Z_2$ each represent general formula (2) or (3);

(2)

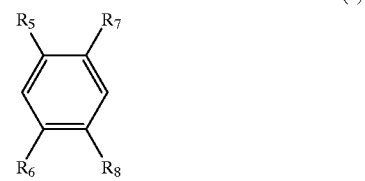

(3)

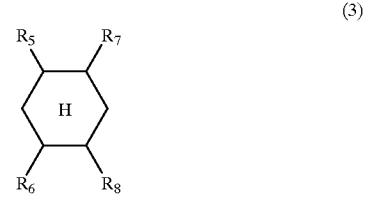

wherein $R_5$ to $R_8$ each represent a hydrogen atom or an alkyl group having 1 to 6 carbon atoms, produced by:

hydrogenating from 10% to 90% of the aromatic groups in an aromatic epoxy compound represented by general formula (4);

(4)

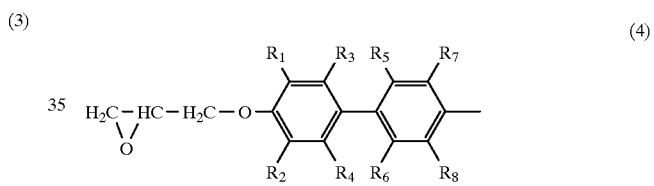

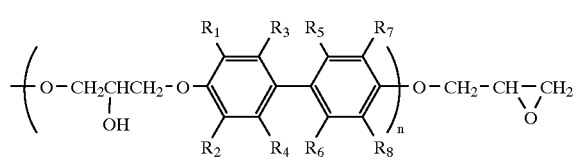

wherein $R_1$ to $R_8$ each represent a hydrogen atom or an alkyl group having 1 to 6 carbon atoms and n represents an integer of 0 to 6.

14. The epoxy compound as claimed in claim 13, wherein the aromatic epoxy compound represented by general formula (4) is dissolved in an ether-based solvent, and the resulting mixture is hydrogenated under pressure in the presence of a catalyst in which rhodium or ruthenium is carried on a graphite.

15. The epoxy compound as claimed in claim 13, wherein from 20 to 90% of the aromatic groups are hydrogenated.

16. The epoxy compound as claimed in claim 15, wherein $R_1$, $R_2$, $R_7$ and $R_8$ each represent a hydrogen atom or a methyl group; $R_3$, $R_4$, $R_5$ and $R_6$ each represent a hydrogen atom and n represents an integer of 0 to 3.

* * * * *